US010780214B1

United States Patent
Hensler

(10) Patent No.: US 10,780,214 B1
(45) Date of Patent: Sep. 22, 2020

(54) IMPLANTABLE MEDICAL DELIVERY DEVICE SECURING EXCESS CATHETER TUBING

(71) Applicant: H & M INNOVATIONS, LLC, Wilmington, NC (US)

(72) Inventor: Robert Sean Hensler, Wilmington, NC (US)

(73) Assignee: H & M Innovations, LLC, Wilmington, NC (US)

( * ) Notice: Subject to any disclaimer, the term of this patent is extended or adjusted under 35 U.S.C. 154(b) by 741 days.

(21) Appl. No.: 14/520,212

(22) Filed: Oct. 21, 2014

Related U.S. Application Data

(60) Provisional application No. 61/894,507, filed on Oct. 23, 2013.

(51) Int. Cl.
| A61M 5/142 | (2006.01) |
| A61M 25/02 | (2006.01) |
| A61M 5/14 | (2006.01) |
| A61M 39/08 | (2006.01) |

(52) U.S. Cl.
CPC ........ A61M 5/14244 (2013.01); A61M 5/142 (2013.01); A61M 25/02 (2013.01); *A61M 5/1413* (2013.01); *A61M 39/08* (2013.01); *A61M 2025/028* (2013.01)

(58) Field of Classification Search
CPC .............. A61M 5/1413; A61M 5/1418; A61M 5/14244–2005/14284; A61M 2205/04; A61M 2209/08–088; A61M 39/08; A61M 25/02; A61M 5/142; A61M 2025/028
See application file for complete search history.

(56) References Cited

U.S. PATENT DOCUMENTS

| 7,216,665 | B1 * | 5/2007 | Sims, Jr. ............... | A61M 39/08 137/355.19 |
| 2005/0063847 | A1 * | 3/2005 | Fathallah ............ | A61M 5/1418 417/477.2 |
| 2006/0065772 | A1 * | 3/2006 | Grant ................... | A61M 5/1418 242/388.6 |
| 2007/0142785 | A1 * | 6/2007 | Lundgaard .......... | A61M 5/1418 604/179 |
| 2009/0171269 | A1 * | 7/2009 | Jennewine ........ | A61M 5/14244 604/67 |

(Continued)

FOREIGN PATENT DOCUMENTS

WO    WO96/35472    * 11/1996

*Primary Examiner* — Lauren P Farrar
*Assistant Examiner* — Laura C Schell
(74) *Attorney, Agent, or Firm* — Chad D. Tillman; Jeremy C. Doerre; Tillman Wright, PLLC

(57) ABSTRACT

A medication delivery device—preferably designed and configured to be implantable for use inside of a human body—secures excess tubing of a catheter to a pump housing. The tubing is received and retained in channels, whereby an excess extent of the catheter that is unneeded can be safely stored in an out-of-the-way position. The channels are defined in and integrally formed with the pump housing. Alternatively, the channels are defined in a catheter retention member that clips onto other otherwise attaches to the pump housing. In the alternative design, the catheter retention member may be provided separately from or provided with the pump and catheter.

16 Claims, 20 Drawing Sheets

(56) References Cited

U.S. PATENT DOCUMENTS

| | | | | |
|---|---|---|---|---|
| 2009/0275896 | A1* | 11/2009 | Kamen | G05D 7/0647 604/151 |
| 2012/0150123 | A1* | 6/2012 | Lawrence | A61M 5/158 604/180 |
| 2013/0178836 | A1* | 7/2013 | Teutsch | A61M 39/08 604/533 |
| 2014/0378891 | A1* | 12/2014 | Searle et al. | A61M 5/14248 604/22 |
| 2015/0343193 | A1* | 12/2015 | Grant | A61M 5/1418 206/389 |

* cited by examiner

FIG. 10a
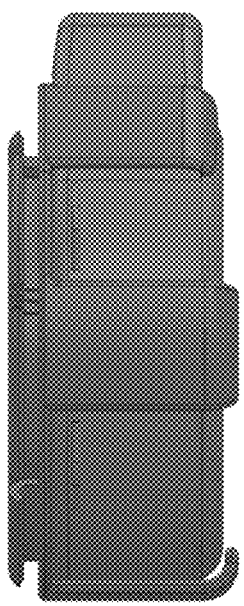
FIG. 11a
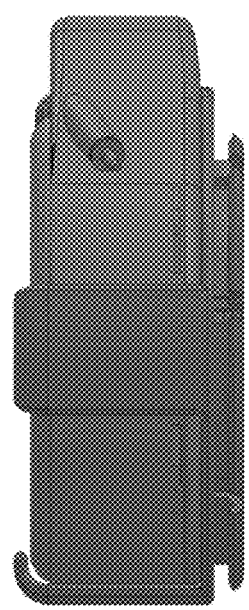
FIG. 12a
FIG. 13a
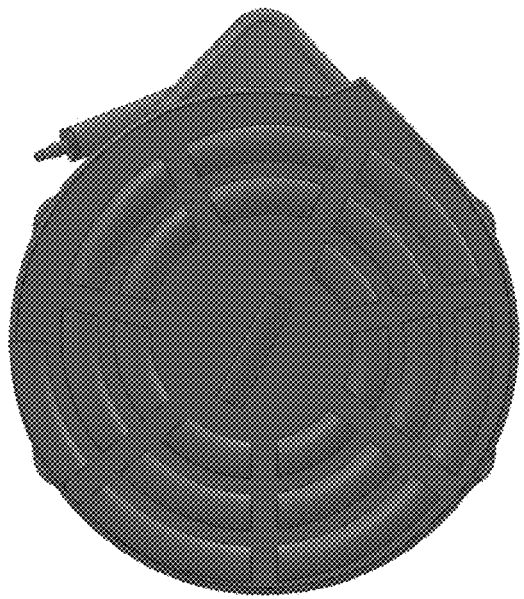
FIG. 14a
FIG. 15a
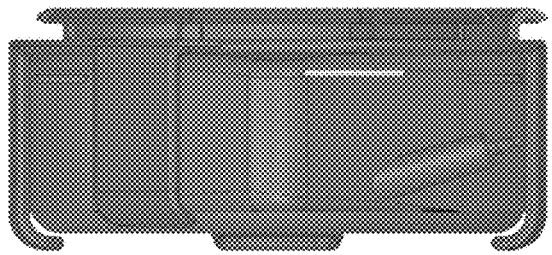
FIG. 16a
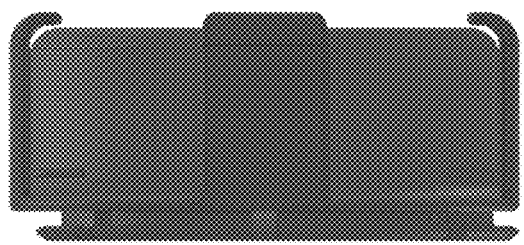

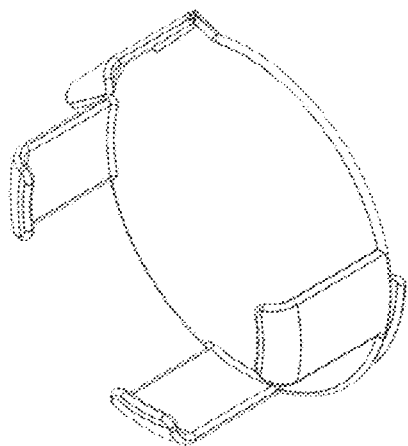
FIG. 17
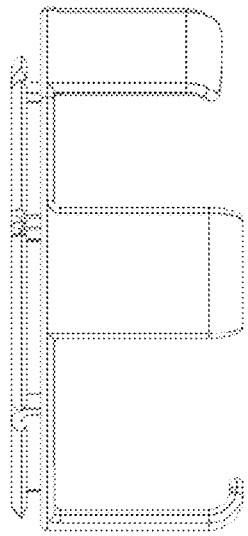
FIG. 18
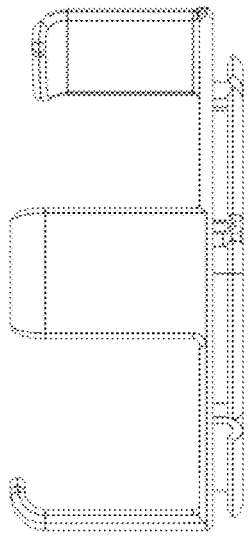
FIG. 19
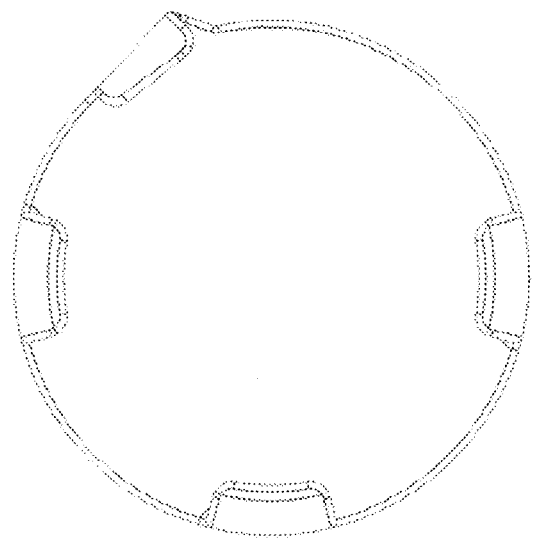
FIG. 20
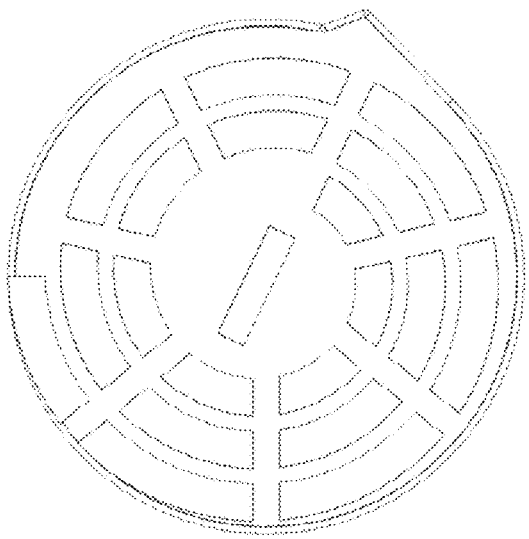
FIG. 21
FIG. 22
FIG. 23
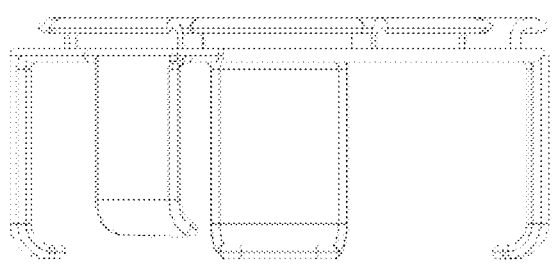
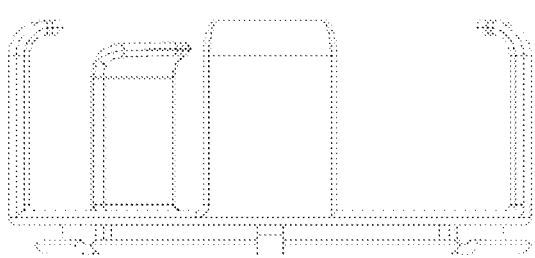

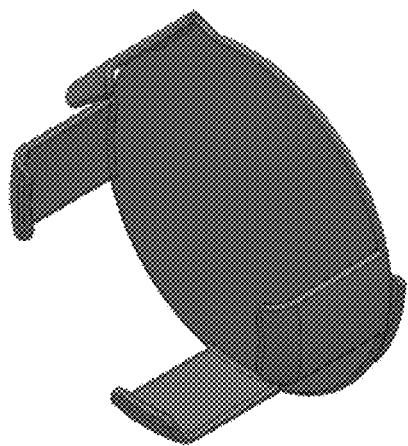
FIG. 17a
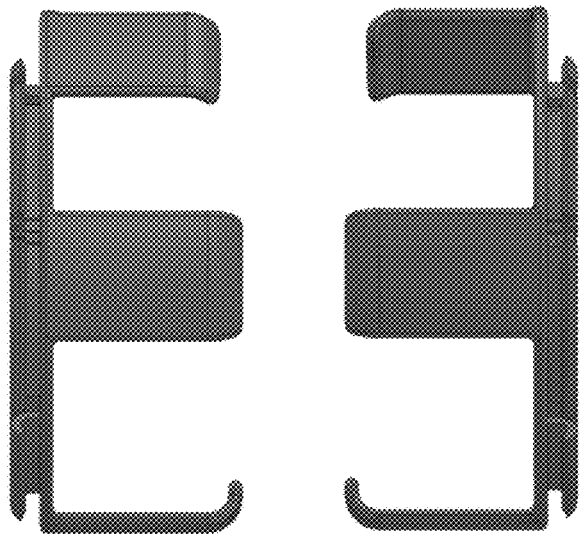
FIG. 18a  FIG. 19a
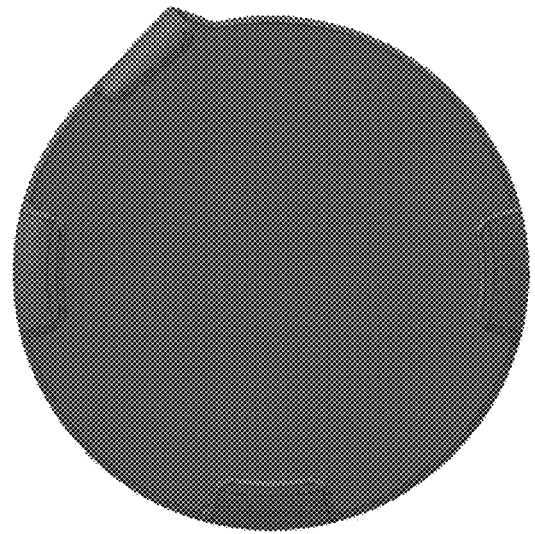
FIG. 20a
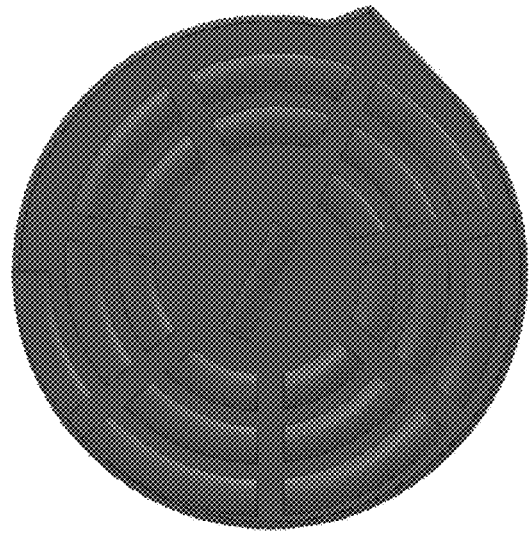
FIG. 21a
FIG. 22a
FIG. 23a
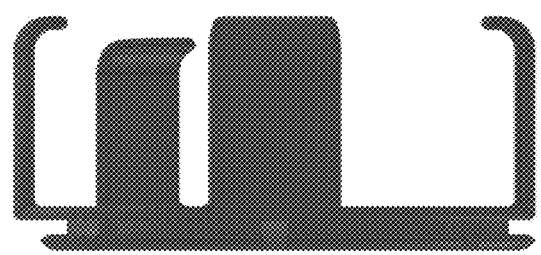

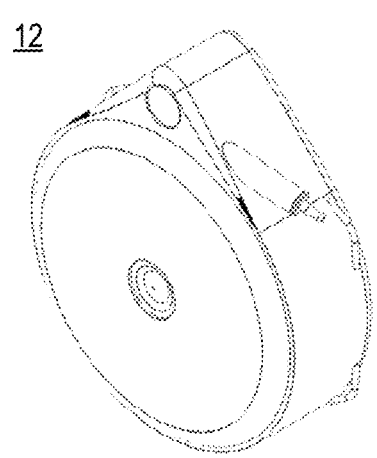
FIG. 24
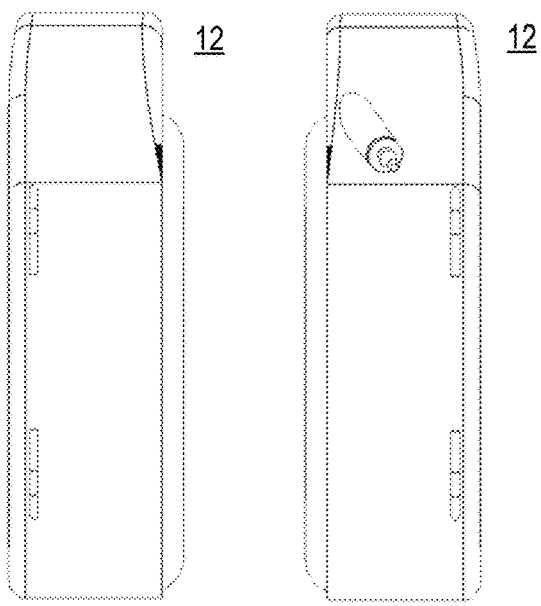
FIG. 25  FIG. 26
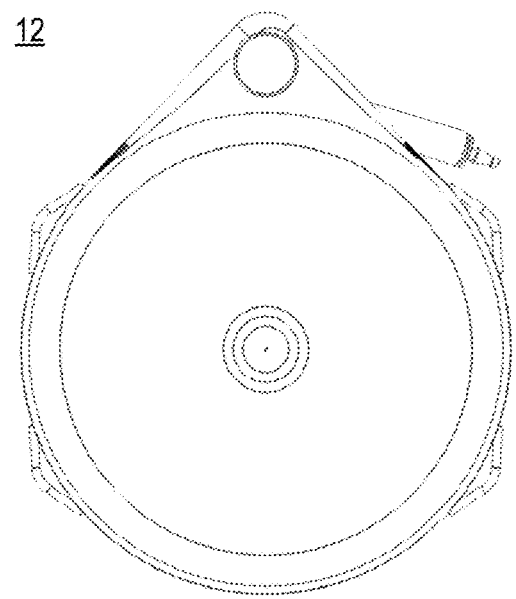
FIG. 27
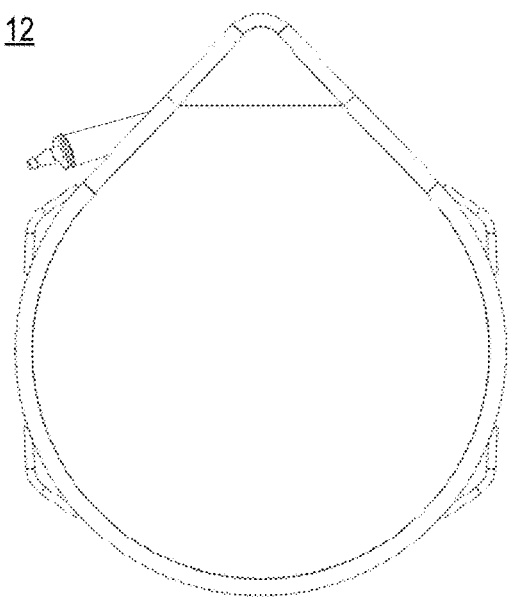
FIG. 28
FIG. 29  FIG. 30
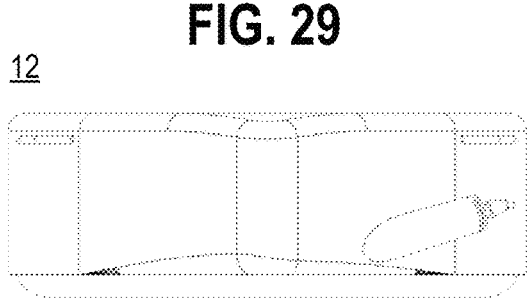

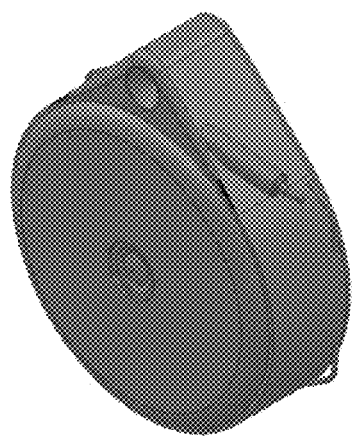
FIG. 24a
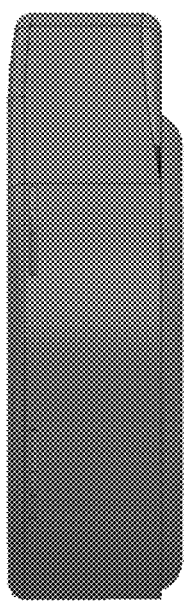
FIG. 25a
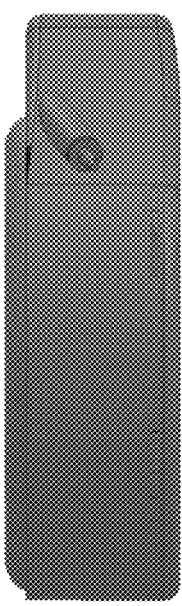
FIG. 26a
FIG. 27a
FIG. 28a
FIG. 29a
FIG. 30a

FIG. 33a
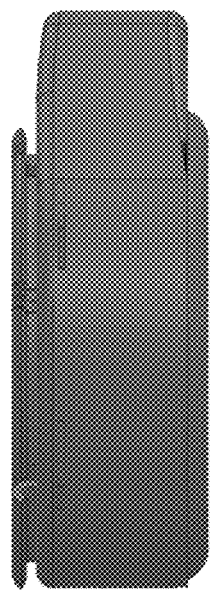
FIG. 34a
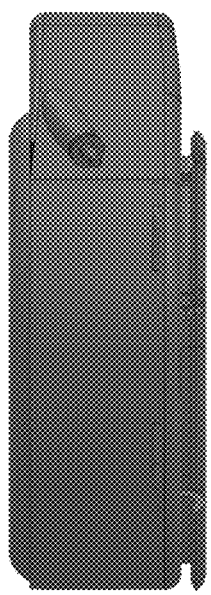
FIG. 35a
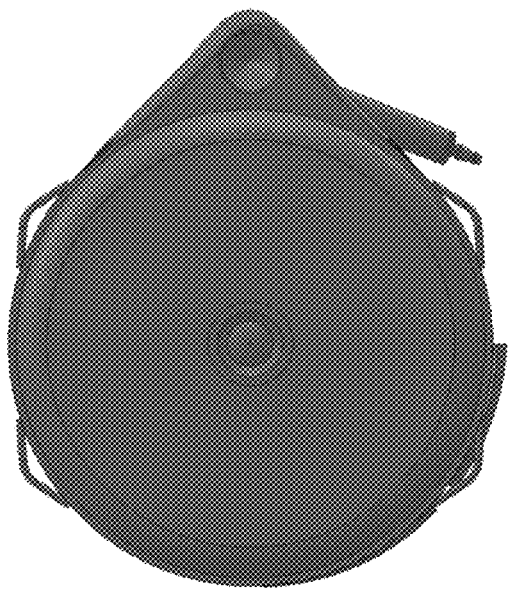
FIG. 36a
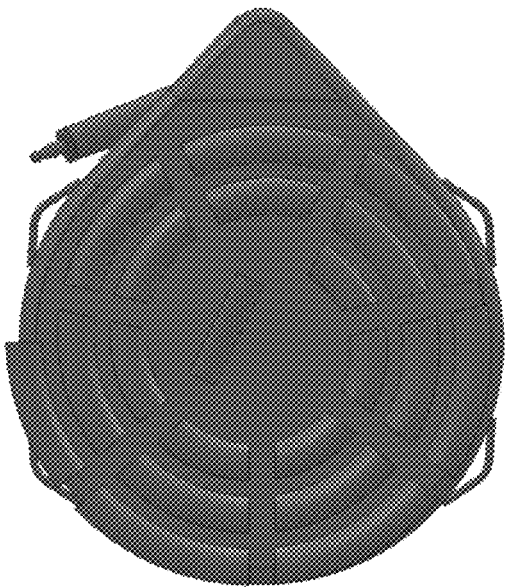
FIG. 37a
FIG. 38a
FIG. 39a
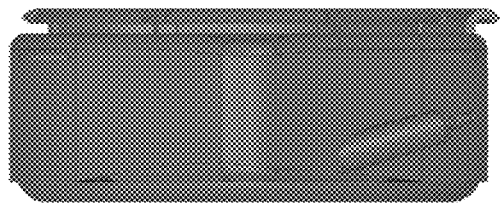
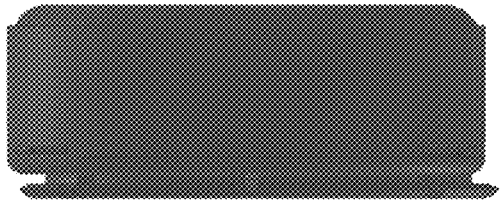

IMPLANTABLE MEDICAL DELIVERY DEVICE SECURING EXCESS CATHETER TUBING

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

COMPUTER PROGRAM LISTING

Submitted concurrently herewith via the USPTO's electronic filing system, and incorporated herein by reference, are computer program files including instructions, routines, and/or other contents of several computer program. A table setting forth the name and size of files included in the computer program listing is included below.

| File Name | Creation Date | File Size (bytes) |
|---|---|---|
| ASCIFY.TXT | Oct. 18, 2013 14:42 | 37473 |
| HENS.TXT | Oct. 18, 2013 14:42 | 1197295 |
| README.TXT | Oct. 18, 2013 14:42 | 2582 |

One of these files, "readme.txt", contains instructions for extracting information from another of the files. This other file represents a compressed binary file that has been converted to ascii format. This file can be converted back to a compressed .zip archive utilizing an assembly conversion program source code for which is contained in "ascify.txt". The readme file includes instructions for compiling and running this conversion program, and instructions for converting the other text files to a compressed, binary file. This compressed, binary file includes an eDrawings™ file representing a computer model. This file can be opened using free eDrawings™ software available from SolidWorks Corp. (www.solidworks.com) for viewing such files.

BACKGROUND

The present invention relates generally to a medical device and, in particular, to a medication delivery device that secures tubing.

Use of implantable pumps for delivering medication to a target anatomical area has become a widely accepted practice. The two main categories of medical pumps include programmable and constant flow pumps. Both types of pumps use an indwelling catheter to establish a pathway from the implantable pump to a desired anatomical area. The desired anatomical area may include, but is not limited to, the epidural and intrathecal space of the spine. Typically, excess catheter is wrapped and stored under the implanted pump. Some of the reported complications dealing with catheter usage include kinking or malposition of the excess catheter. The delivery of medication fails if the catheter is impeded.

Accordingly, it is believed that a need exists for the safe storage of excess catheter without the concern of impeding or obstructing kinks. Additionally, it is believed that a need exists for the safe storage of excess catheter while threading a suture material through a tissue wall surrounding an incision, through the incision, and withdrawing the suture material back through the tissue wall without the concern of threading or impacting an indwelling catheter. It is believed that one or more of these needs and other needs are addressed by one or more aspects and features of the present invention.

SUMMARY OF THE INVENTION

Broadly defined, the present invention relates to catheter securing apparatus, methods and systems and, in particular, to a catheter securing apparatus, methods and systems for storing excess catheter quickly and efficiently during surgery.

In a first aspect of the present invention, a medication delivery device that secures tubing comprises a housing containing a pump configured to deliver medicine in the form of a fluid; a catheter extending from the pump and exterior to the housing and defining a fluid pathway for delivering the fluid to a desired anatomical location; a catheter retention member configured to receive and retain an extent of the catheter, whereby an excess extent of the catheter that is unneeded can be safely stored in an out-of-the-way position; and at least one extension wall—and preferably at least two extension walls—configured to clip the catheter retention member onto the pump housing. The catheter retention member preferably is integrally formed with the at least one extension wall in an injection-molding manufacturing process. The catheter retention member also preferably defines channels dimensioned to receive and retain tubing of the catheter in a frictional fit therein, which channels also preferably are defined in the injection-molding manufacturing process of the catheter retention member.

In another aspect of the present invention, a medication delivery device comprises a housing containing a pump configured to deliver medicine in the form of a fluid; and a catheter extending from the pump and exterior to the housing and defining a fluid pathway for delivering the fluid to a desired anatomical location; wherein the pump housing defines channels dimensioned to receive and retain an extent of tubing of the catheter in a frictional fit therein, whereby an excess extent of tubing of the catheter that is unneeded can be safely stored in an out-of-the-way position. The channels preferably are integrally formed with the pump housing during an injection-molding manufacturing process.

In another aspect, a medication delivery device providing for storage of excess catheter, comprises: a pump configured to deliver a fluid to the body, wherein the pump includes a front, a back, and a side wall; a catheter defining a pathway for delivery of the fluid from the pump to a desired anatomical location; a cover having a front surface and a back surface; and at least one extension wall extending from the cover and configured to secure the cover onto the pump such that the cover may be detached from and reattached to the pump. The cover includes one or more channels each configured and dimensioned to receive and retain therein an extent of tubing of the catheter.

In a feature of this aspect, the pump comprises a septum located on a front side for accessing a chamber for holding the fluid. The cover preferably is positioned such that septum is not obstructed.

In a feature of this aspect, the pump comprises a stem to connect the pump to the catheter. The stem preferably is angled to direct the catheter tubing to the one or more channels.

In another feature, the one or more channels are located on a front of the cover.

In another feature, the one or more channels are configured in a spiral configuration.

In another feature, the channels are dimensioned to receive tubing of the catheter in a frictional fit therein.

In another feature, the one or more channels are defined by structure formed from a flexible and resilient material and demonstrates resiliency and flexibility when tubing of the catheter is inserted therein.

In another feature, a back surface of the cover abuts a back surface of a housing of the pump when the cover is secured to the pump by the at least one extension wall. T back surface of the cover may be planar, and the back surface of the pump housing may be planar.

In another feature, the cover is made from a flexible and resilient material and demonstrates resiliency and flexibility when the cover is secured to and removed from the pump. The cover may be mounted to the pump by flexing and bending of the cover.

In another feature, extension wall comprises an L-shaped clip. The at least one extension wall may comprise two opposed L-shaped clips, each extending a length spanning the depth of the pump housing extending between a front and a back of the pump housing. When mounted, the extension wall preferably is positioned such that stem is not obstructed.

In another aspect, a catheter retention device providing for the storage of excess catheter used with an implantable medical delivery pump comprises: a cover having a front surface and a back surface; at least one extension wall to secure the cover to the pump with the back surface of the cover abutting a back surface of the pump; and one or more channels configured to receive and retain the catheter to the cover.

In a feature, the one or more channels are formed in the front surface of the cover.

In a feature, the one or more channels are dimensioned such that the excess catheter is received and retained in a frictional fit within the one or more channels.

In a feature, the one or more channels are arranged in a spiral configuration.

In a feature, the one or more channels are defined by structure formed from a flexible and resilient material and demonstrates resiliency and flexibility when tubing of the catheter is inserted therein.

In a feature, the cover is made from a flexible and resilient material and demonstrates resiliency and flexibility when the cover is secured to and removed from the pump. The act of mounting the cover to the pump may include flexing and bending of the cover. The pump preferably comprises a rigid housing or casing.

In another feature, an extension wall comprises a resilient and flexile clip.

In another feature, an extension wall comprises a clip.

In another feature, the at least one extension wall comprises two opposed L-shaped clips.

In another feature, the at least one extension wall extends a length from the cover that spans a depth of the pump extending between a front and a back of the pump. The at least one extension wall may comprise two opposed L-shaped clips, with ends of the clips abutting a front of the pump and with a back of the cover abutting a back of the pump.

In another aspect, a medication delivery device providing for the storage of excess catheter, comprises: a pump housing having a front surface, a backs surface, and a side surface; and one or more channels configured to receive and retain excess catheter tubing to the pump housing.

In a feature, the one or more channels are oriented in a spiral configuration.

In a feature, the one or more channels are configured to receive the excess catheter tubing in a frictional fit therein.

In a feature, the opening is smaller than the diameter of the catheter so that the catheter may be forced into at least one of the one or more channels and retained. The one or more channels preferably are flexible and resilient so as to receive the catheter but have sufficient stiffness or rigidity to retain the catheter in a frictional fit therein.

In another aspect, a method of installing a medication delivery device comprises the steps of: providing a pump having a septum and a stem, a catheter having tubing, and a catheter securing device having a flexible cover, the cover including one or more channels on a surface of the cover and clips for attachment of the cover to the pump; mounting the catheter securing device onto the pump; inserting an extent of excess catheter tubing into the one or more channels of the cover; attaching one end of the catheter tubing to the stem of the pump; and inserting the pump into a body such that the excess extent of catheter tubing received within the one or more channels remains in the one or more channels.

Another aspect of the invention comprises a catheter securing device as disclosed herein.

Another aspect of the invention comprises a catheter securing device system as disclosed herein.

Another aspect of the invention comprises a method of installing a catheter securing device as disclosed herein.

In still yet another aspect, a catheter securing device for the storage of excess catheter comprises at least one extension wall configured to attach to a pump housing of a medication delivery device; and one or more channels dimensioned to receive and retain an excess extent of tubing of the catheter of the medication delivery device.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

Further areas of applicability of the present invention, as well as additional aspects and features, will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

One or more preferred embodiments of the present invention now will be described in detail with reference to the accompanying drawings.

FIG. 10a is a perspective shaded view of the medical delivery device of FIG. 2.

FIG. 11a is a first shaded side elevational view of the medical delivery device of FIG. 10.

FIG. 12a is a second shaded side elevational view of the medical delivery device of FIG. 10, the view being opposite to the view of FIG. 11.

FIG. 13a is a front shaded plan view of the medical delivery device of FIG. 10.

FIG. 14a is a back shaded plan view of the medical delivery device of FIG. 10.

FIG. 15a is a top shaded plan view of the medical delivery device of FIG. 10.

FIG. 16a is a bottom shaded plan view of the medical delivery device of FIG. 10.

FIG. 17 is a perspective view of the catheter securing device of the medical delivery device of FIG. 10.

FIG. 17a is a perspective view of the catheter securing device of the medical delivery device of FIG. 10.

FIG. 18 is a first side elevational view of the catheter securing device of FIG. 17.

FIG. 18a is a first shaded side elevational view of the catheter securing device of FIG. 17a.

FIG. 19 is a second side elevational view of the catheter securing device of FIG. 17, the view being opposite to the view of FIG. 18.

FIG. 19a is a second shaded side elevational view of the catheter securing device of FIG. 17, the view being opposite to the view of FIG. 18a.

FIG. 20 is a front plan view of the catheter securing device of FIG. 17.

FIG. 20a is a front shaded plan view of the catheter securing device of FIG. 17a.

FIG. 21 is a back plan view of the catheter securing device of FIG. 17.

FIG. 21a is a back shaded plan view of the catheter securing device of FIG. 17a.

FIG. 22 is a top plan view of the catheter securing device of FIG. 17.

FIG. 22a is a top shaded plan view of the catheter securing device of FIG. 17a.

FIG. 23 is a bottom plan view of the catheter securing device of FIG. 17.

FIG. 23a is a bottom shaded plan view of the catheter securing device of FIG. 17a.

FIG. 24 is a perspective view of the pump of the medical delivery device of FIG. 10.

FIG. 24a is a perspective shaded view of the pump of FIG. 10a.

FIG. 25 is a first side elevational view of the pump of FIG. 24.

FIG. 25a is a first shaded side elevational view of the pump of FIG. 24a.

FIG. 26 is a second side elevational view of the pump of FIG. 24, the view being opposite to the view of FIG. 25.

FIG. 26a is a second shaded side elevational view of the pump of FIG. 24a, the view being opposite to the view of FIG. 25a.

FIG. 27 is a front plan view of the pump of FIG. 24.

FIG. 27a is a front shaded plan view of the pump of FIG. 24a.

FIG. 28 is a back plan view of the pump of FIG. 24.

FIG. 28a is a back shaded plan view of the pump of FIG. 24a.

FIG. 29 is a top plan view of the pump of FIG. 24.

FIG. 29a is a top shaded plan view of the pump of FIG. 24a.

FIG. 30 is a bottom plan view of the pump of FIG. 24.

FIG. 30a is a bottom shaded plan view of the pump of FIG. 24a.

FIG. 32a is a perspective view of the pump and catheter securing device shown in FIG. 31a.

FIG. 33a is a perspective shaded view of the pump of FIG. 10a.

FIG. 34a is a first shaded side elevational view of the pump of FIG. 24a.

FIG. 35a is a second shaded side elevational view of the pump of FIG. 24a, the view being opposite to the view of FIG. 25a.

FIG. 36a is a front shaded plan view of the pump of FIG. 24a.

FIG. 37a is a back shaded plan view of the pump of FIG. 24a.

FIG. 38a is a top shaded plan view of the pump of FIG. 24a.

FIG. 39a is a bottom shaded plan view of the pump of FIG. 24a.

DETAILED DESCRIPTION

Figure 1:
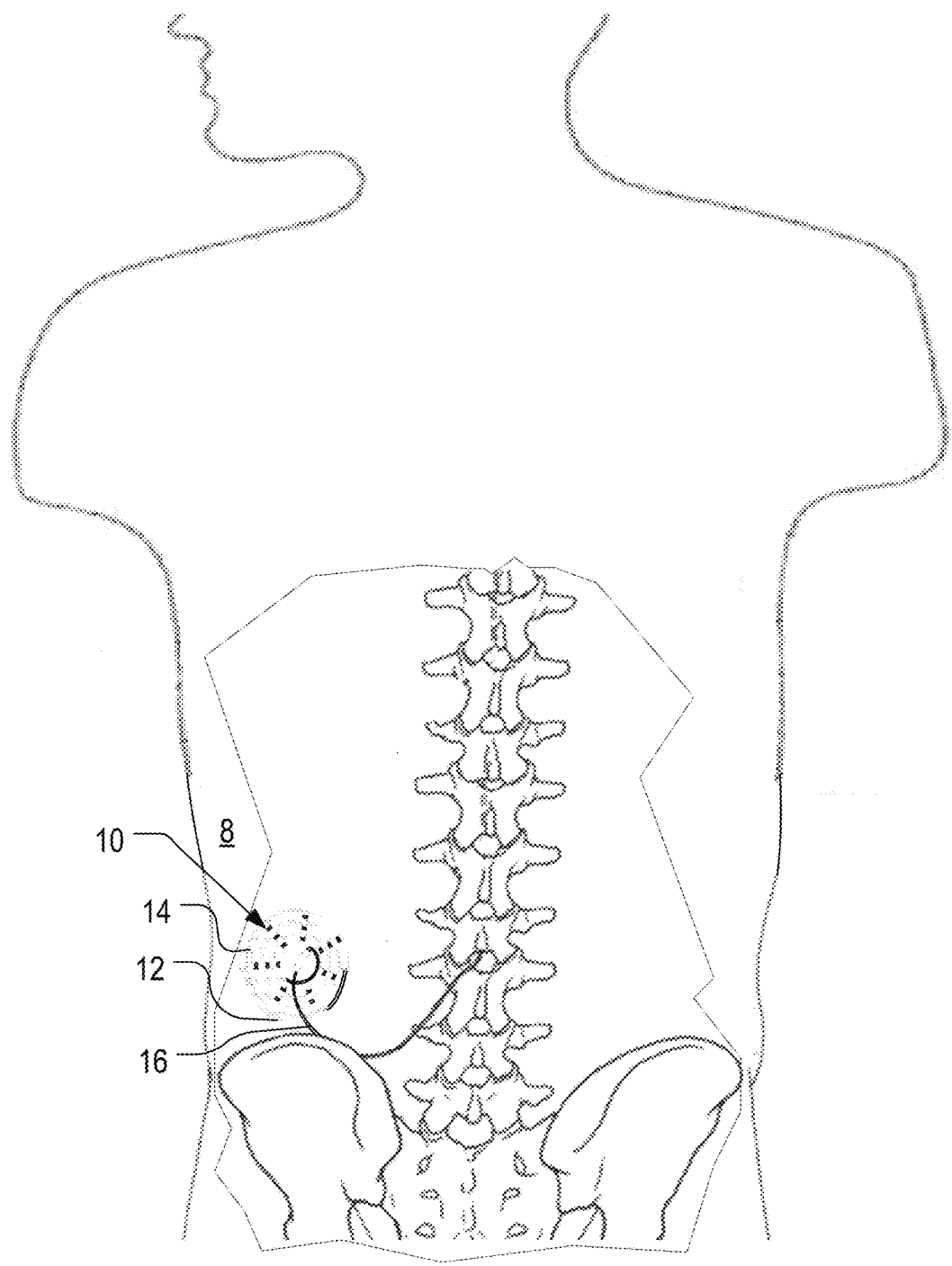
FIG. 1 is a partially cutaway front view of an abdominal wall with an implanted medical delivery device in accordance with one or more preferred embodiments of the present invention.

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers," "a picnic basket having crackers without cheese," and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its application, or uses.

FIG. 1 is a partially cutaway front view of an abdominal wall 8 of a person's body, in which a medical delivery device 10 in accordance with a preferred embodiment of the invention has been inserted. As described in greater detail below, the medical delivery device 10 includes a pump 12, a catheter securing device 14, and a catheter 16. As shown, the catheter 16 travels subcutaneously to enter the spinal canal. In an alternative embodiment, the catheter 16 travels to another targeted anatomical area.

Figure 2:
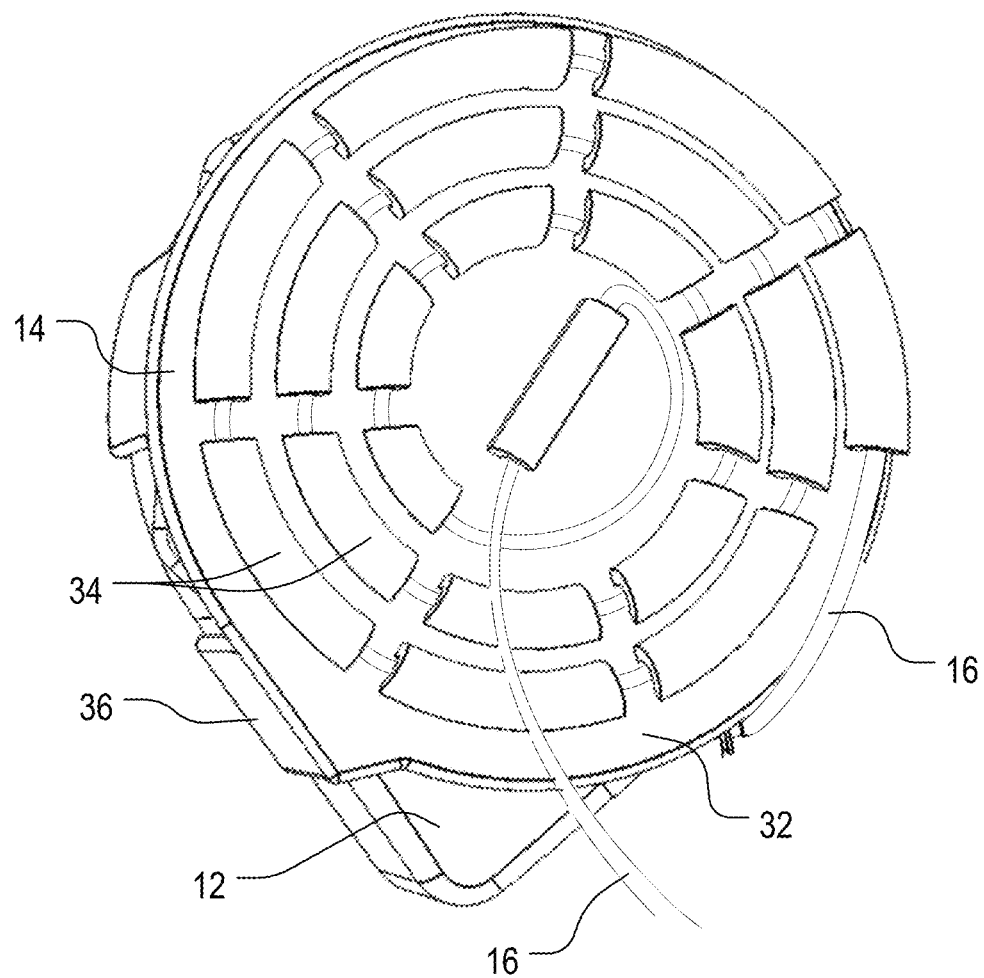
FIG. 2 is a front perspective view of a medical delivery device in accordance with a preferred embodiment of the present invention, wherein an extent of catheter tubing is received and retained.
Figure 3:
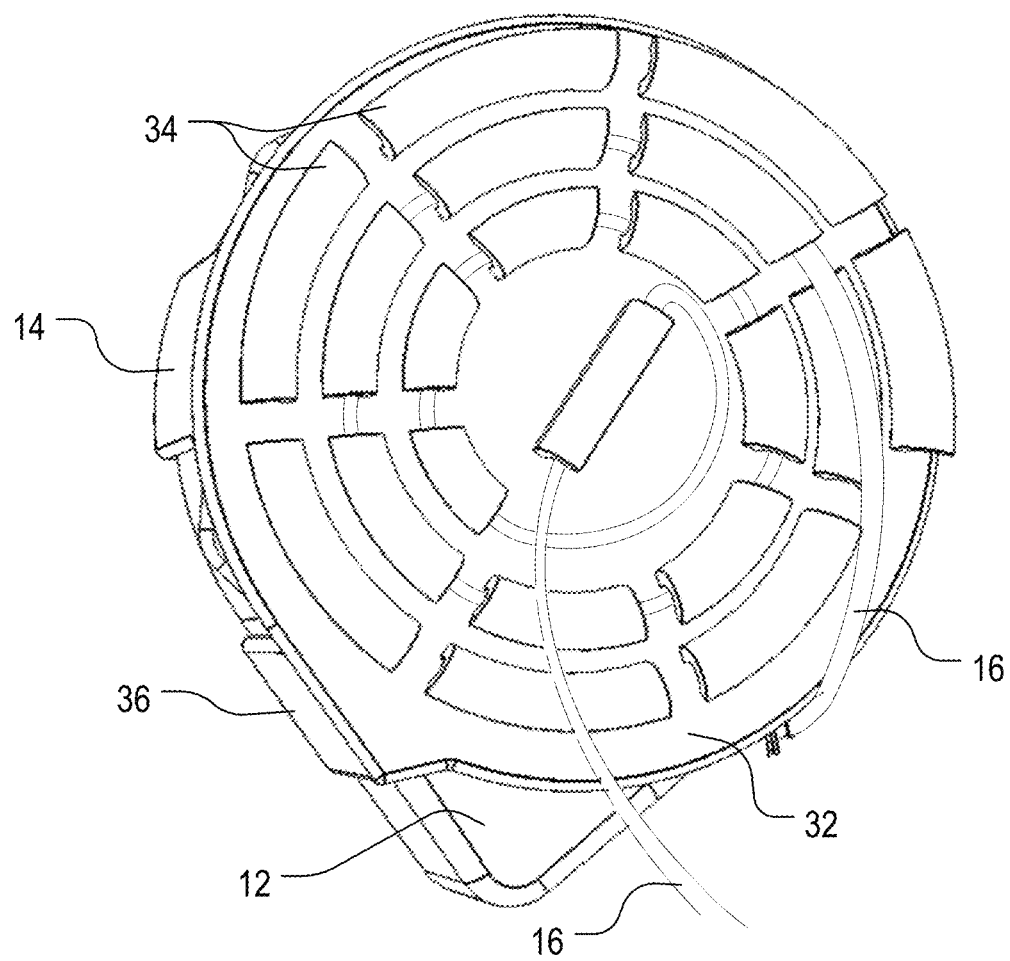
FIG. 3 is another front perspective view of the medical delivery device of FIG. 2, wherein a lesser extent of catheter tubing is received and retained.

FIGS. 2 and 3 are front perspective views of the pump 12, the catheter securing device 14, and the catheter 16 of the medical delivery device 10 of FIG. 1. As shown in FIGS. 2 and 3, the catheter securing device 14 attaches to the pump 12 with excess catheter 16 being secured to the catheter securing device 14. A maximum extent of the excess catheter 16 is secured to the catheter securing device 14 in FIG. 2, with the catheter 16 extending the full distance along a spiral pathway from edge to center of the device 14. In contrast, an intermediate extent of the excess catheter 16 is secured to the catheter securing device 14 in FIG. 3, with the catheter 16 extending only a partial distance along the spiral pathway of the device 14 and omitting the outermost radial segment.

Figure 4:
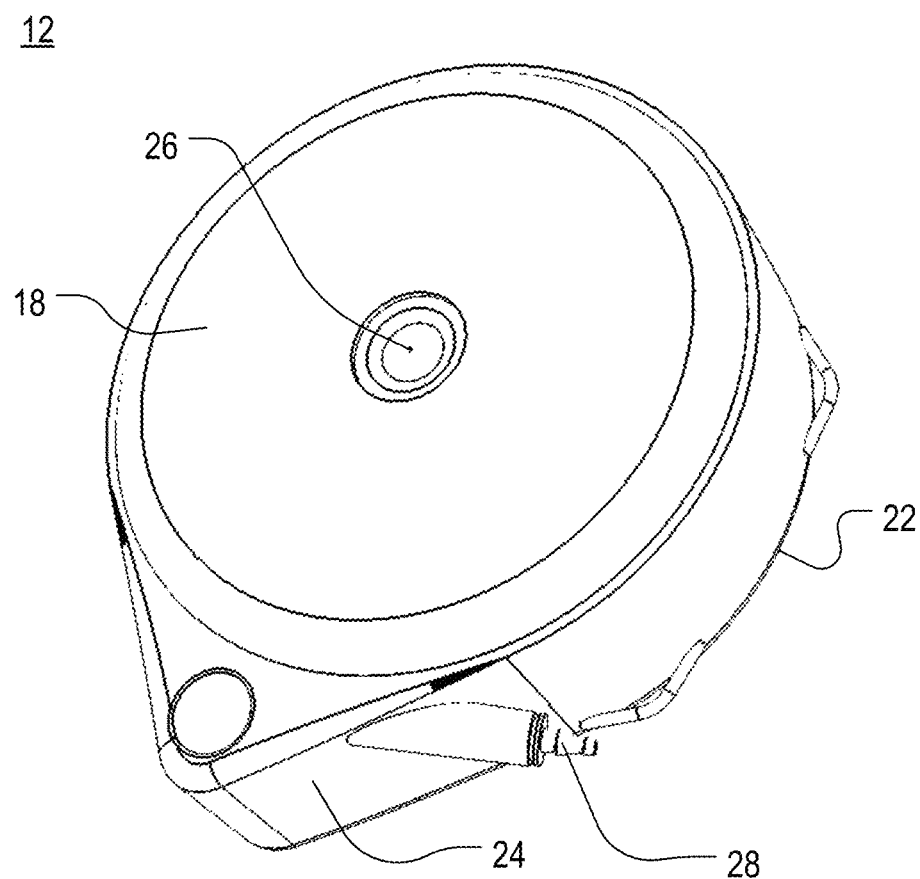
FIG. 4 is a perspective view of the medical delivery device of the pump of FIG. 2.

FIG. 4 is a perspective view of the pump 12 of FIG. 1. As shown in FIG. 4, the pump 12 includes a front surface 18, a back surface 22, and at least one side wall 24. The pump 12 could be any suitable pump for use with the catheter securing device 14 that is implanted subcutaneously to deliver medicine in the form of a fluid to the body. The front surface 18 of the pump 12 may include a septum 26 to access a chamber (not shown) which holds fluids including, but is not limited to, medicine to be dispensed within the body. The at least one side wall 24 of the pump 12 may include a stem 28 for attachment of the catheter 16 to the pump 12. Generally, the pump 12 releases fluids continuously or at predetermined intervals. Fluid is released at stem 28 and travels through the connected catheter 16 to a desired anatomical area. As shown in FIGS. 4, the stem 28 is curved to conform to the shape of the pump 12 so that the overall profile of the pump 12 is minimized. In other contemplated embodiments, the stem 28 is angled or shaped to direct the catheter 16 toward the attached catheter securing device 14. For example, the stem 28 may be curved towards the catheter securing device 14. The catheter 16 could be any elongated shaft or tube which is implanted subcutaneously or inserted through a body opening.

Figure 5:
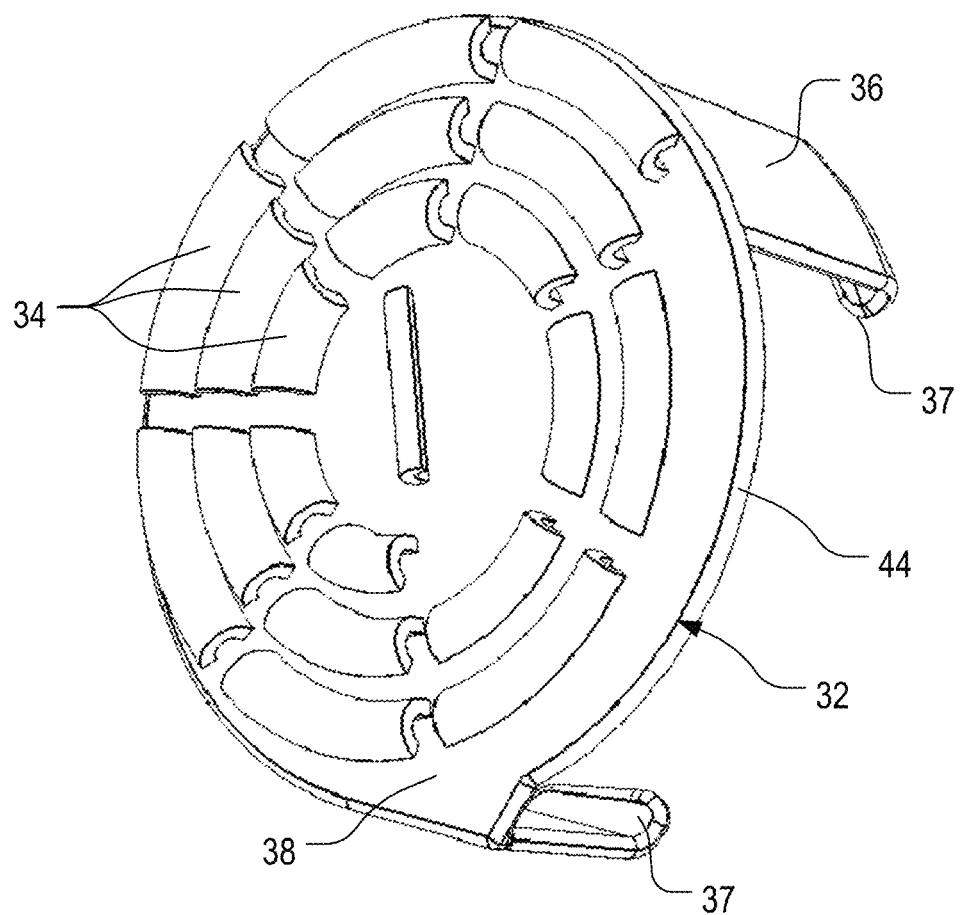
FIG. 5 is a perspective view generally showing a top or front of the catheter retention member (also referred to as a catheter securing device) of the medical delivery device of FIG. 2.

With reference to FIG. 5, the catheter securing device 14 includes a cover 32 with one or more channels 34 and at least one extension wall 36, preferably in the form of a flexible and resilient L-shaped clip or finger. The cover 32 is secured to the pump 12 by the at least one extension wall 36 gripping the front surface 18 of the pump 12 with a distal edge portion 37, with the cover 32 extending across the back surface 22 of the pump 12. A frictional fit may be provided. Furthermore, at least four extension walls 36 with distal edge portions 37 preferably are provided. The one or more channels 34 are located on the cover 32 and are configured to receive and retain the excess catheter 16 and, specifically, excess tubing of the catheter that may be unneeded in a particular case.

In this respect, the catheter securing device 14 allows doctors and nurses to safely store in an out-of-the-way position an excess extent of the catheter 16 quickly and efficiently during surgery. The safe storage of the excess extent of the catheter 16 ensures that the catheter 16 is implanted into a user's body without kinks. The safe storage of the excess extent of catheter 16 further ensures that a suture material may be used to close an incision without impacting the indwelling catheter 16.

Figure 6:
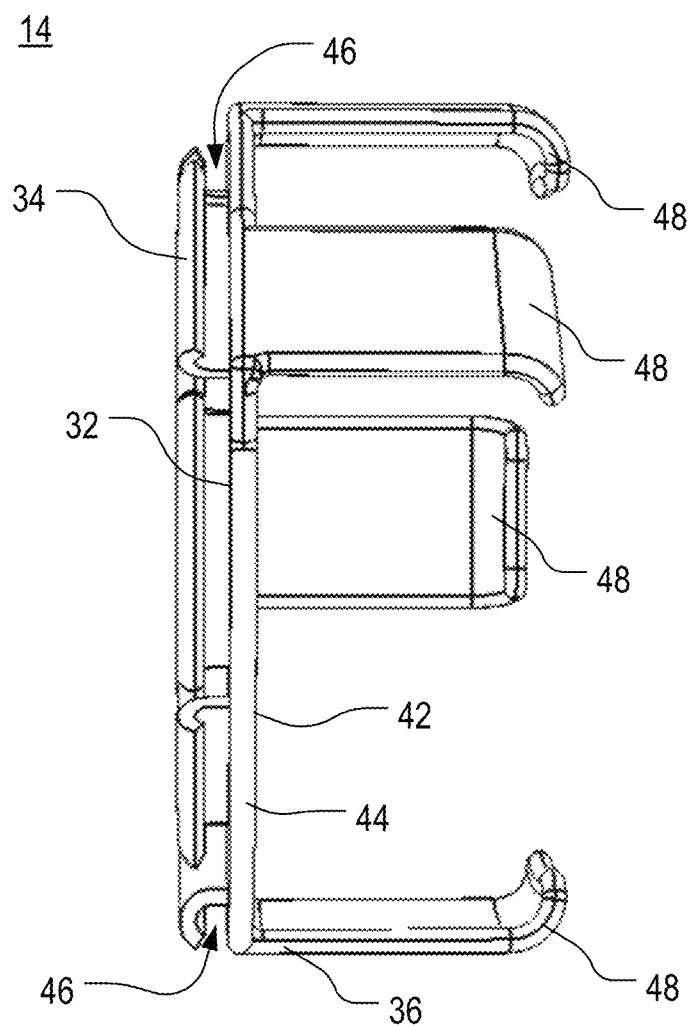
FIG. 6 is a side view of the catheter securing device of FIG. 5.

As shown in FIGS. 5 and 6, the cover 32 includes a front surface 38, a back surface 42 (shown on FIG. 7), and at least one side edge 44. Located on the front surface 38 are one or more channels 34 that are configured and dimensioned to define a recessed area 46 to receive and retain excess extent of the catheter 16 in a frictional-fit engagement.

In particular, and perhaps as best shown in FIG. 6, the one or more channels 34 are configured to have a curved cross-sectional profile defining with a curved, concave recessed opening 46. The radius of the curved recessed opening 46 defined by the channels 34 can vary, but preferably the radius generally is slightly smaller than a radius of curvature of the tubing of the catheter 16 so that the catheter 16 may be forced into and received within at least one of the channels 34 and retained therein by a frictional-fit engagement. Moreover, the structure defining the channels preferably is resilient and flexible and hold the catheter 16 is within the recessed areas 46 in tension.

Figure 40:
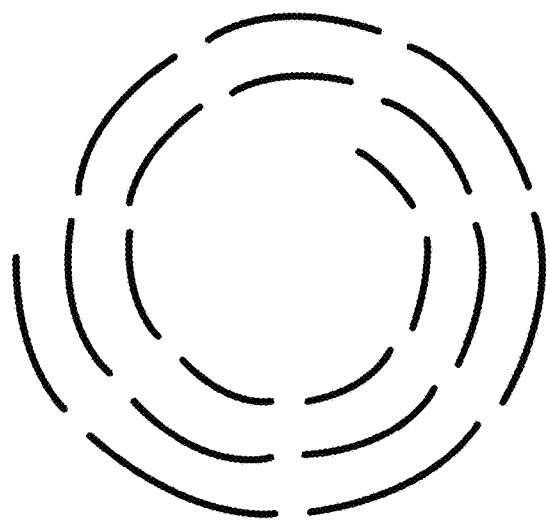
FIG. 40 is a schematic illustration representative of a spiral configuration of channels in a medical delivery device of FIG. 10.
Figure 41:
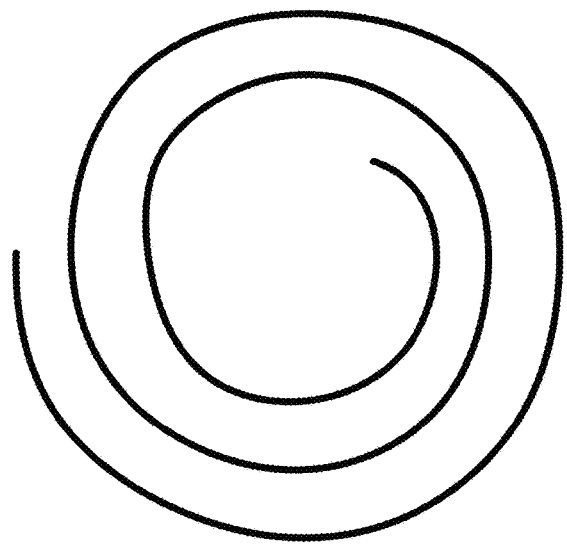
FIG. 41 is a schematic illustration representative of an alternative spiral configuration for a single channel.
Figure 42:
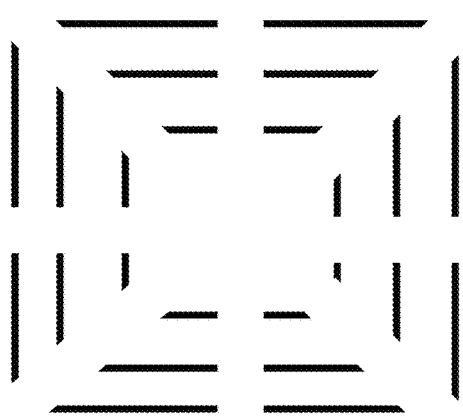
FIG. 42 is a schematic illustration representative of an alternative, rectangular configuration of channels.
Figure 43:
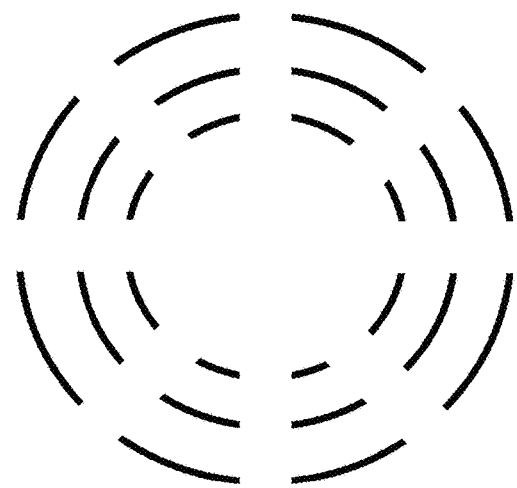
FIG. 43 is a schematic illustration representative of an alternative, oval configuration of channels.

The one or more channels 34 preferably are comprised of sterilizable flexible resilient material which flexes to receive the catheter 16 within the recessed areas 46 but which has sufficient stiffness to hold the catheter 16. In other contemplated embodiments, the one or more channels 34 take on a different shape other than the curved profile and spiral configuration shown. for example, the channels could be arranged in a rectangular configuration or oval configuration, with each channel defining a band with spacing between adjacent channels sufficient to allow the catheter 16 to pass therebetween. Four different illustrative configurations are shown in FIG. 40 through FIG. 43, wherein the configuration of FIG. 40 schematically represents the spiral configuration of the series of channels of the devices of FIGS. 1-39. FIG. 41 schematically illustrates a single channel defining a similar spiral configuration. In contrast, FIG. 42 schematically illustrates a series of channels in an oval configuration, and FIG. 43 illustrates a series of channels in a rectangular configuration.

The excess catheter 16 may occupy all of the one or more channels 34 as shown in FIG. 2, or just some of the one or more channels 34 as shown in FIG. 3. Before or during surgery, the length of the catheter 16 may be extended by removing the catheter 16 from all or some of the one or more channels 34. Furthermore, the length of the catheter 16 may be shortened by adding the catheter 16 to all or some of the one or more channels 34.

The back surface 42 or side wall 44, or both collectively, include extension walls 36 extending therefrom approximately the depth of the pump 12 (as measured between the front and back surface of the pump) so as to hold the pump 12 between the back surface 42 and the distal edge portion 37 of each extension wall 36 and, thereby, retain the catheter securing device 14 and pump 12 together. Additionally, the front surface 18 may include slots or recesses (not shown) for receiving therein respectively a portion of a distal edge portion 37 for collectively securing the catheter securing device 14 to the pump 12.

Figure 7:
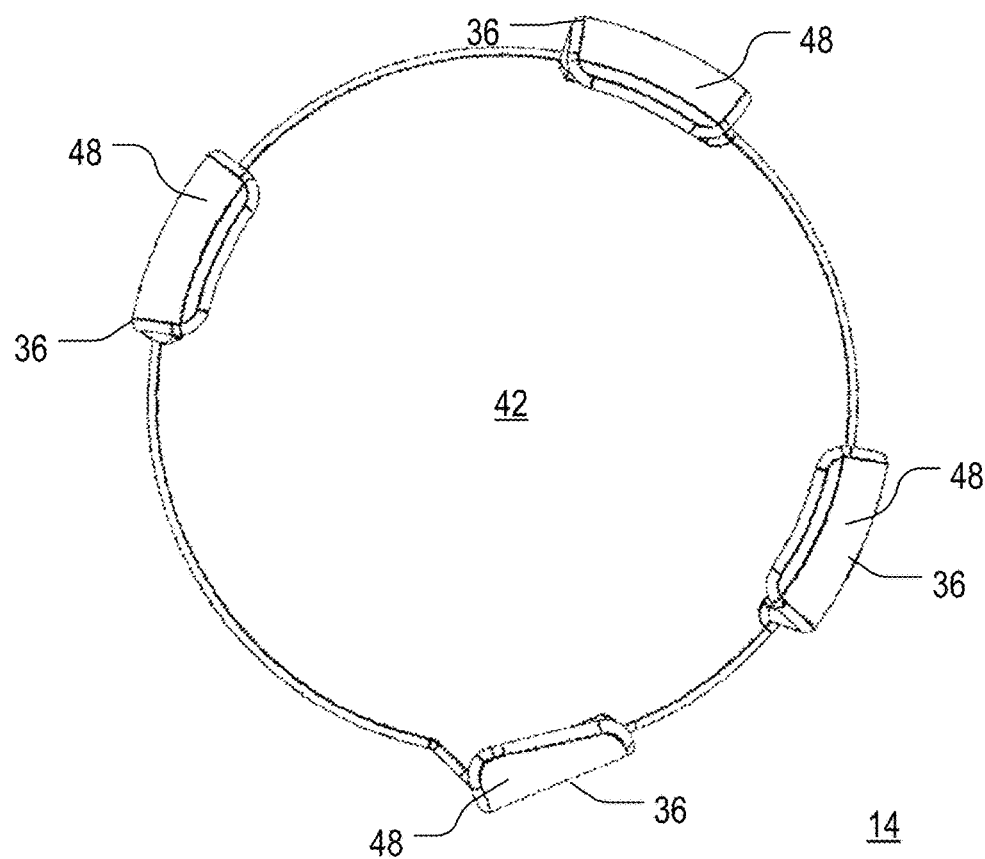
FIG. 7 is a view of a bottom or back of the catheter securing device of FIG. 5.

As shown in FIGS. 6 and 7, the at least one extension wall 36 and distal edge portion 37 define an L-shaped finger 48 extending from the cover 32. In preferred embodiments as shown, there are four L-shaped fingers 48. The at least one L-shaped finger 48 is configured such that one end contacts the front 18 of the pump 12 when the catheter securing device 14 is clipped onto or otherwise attached to the pump 12.

Importantly, the at least one L-shaped finger 48 is positioned such that the distal end does not obstruct the septum 26 of the pump 12 when the catheter securing device 14 is clipped onto the pump 12. Similarly, the at least one L-shaped finger 48 is positioned such that the stem 28 is not obstructed. In other contemplated embodiments, the at least one extension wall 36 can take on various shapes and sizes and it is not confined to the L-shaped finger 48 as shown. Other types of holding devices could be employed to hold the catheter securing device 14 and the pump 12 together, including clamps, C-shaped or U-shaped brackets, etc.

Figure 8A:
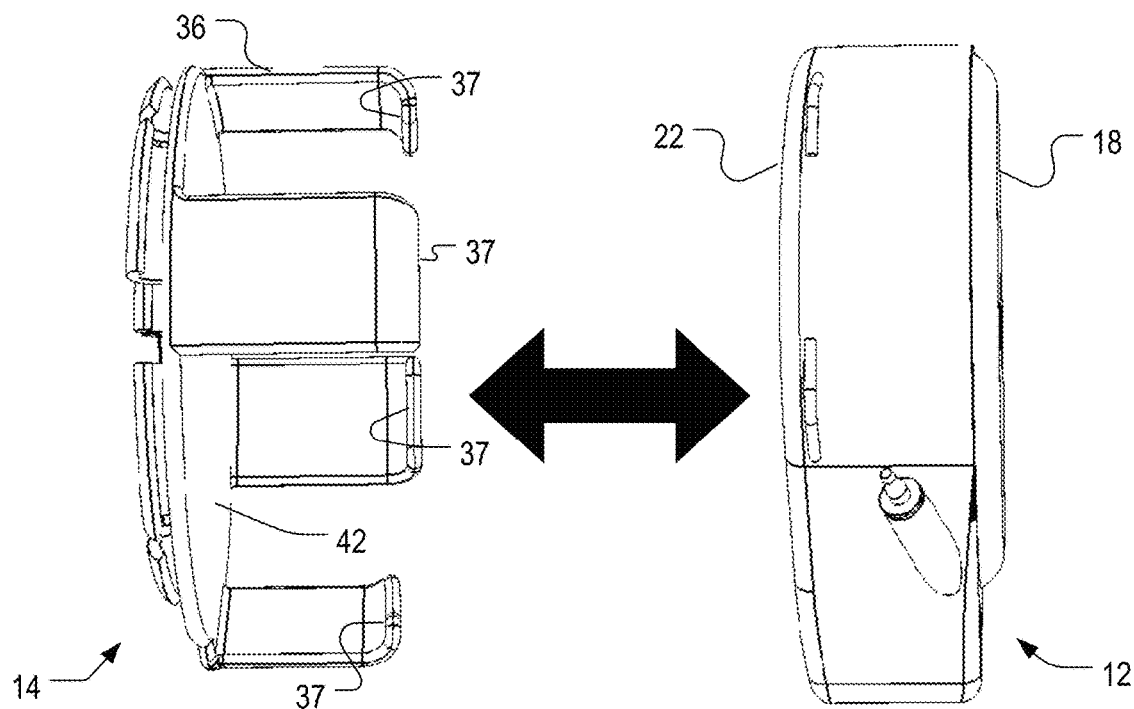
FIG. 8A is a side view of the catheter securing device and the pump of FIG. 3 when separated.
Figure 8B:
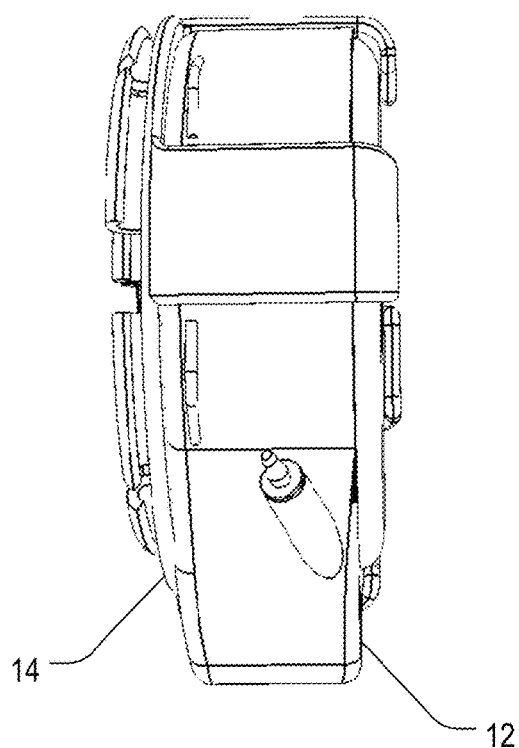
FIG. 8B is another side view of the catheter securing device and the pump of FIG. 3 when secured together.

FIGS. 8A and 8B are side views of the catheter securing device 14 and the pump 12 being connected together. To join or separate the catheter securing device 14 and the pump 12, the cover 32 preferably is flexed or slightly bent and/or the at least one L-shaped finger 48 is flexed or slightly bent. In this respect, the cover 32 and each finger 48 preferably is resilient and flexible, and undergoes elastic deformation during such bending and flexing. The cover 32 and each finger 48 preferably are composed of one or more flexible resilient materials. In at least one contemplated embodiment, the catheter securing device 14 is comprised of flexible resilient plastic or polymer which is able to be sterilized and which undergoes elastic deformation.

In a further contemplated embodiment, the at least one extension wall 36 can be adapted further to connect to various shapes and sizes of pumps other than the pump 12 as shown. In accordance with another embodiment, the at least one extension wall 36 is hinged to the cover 32 such that it rotates open and closed for engaging the pump 12.

Figure 9:
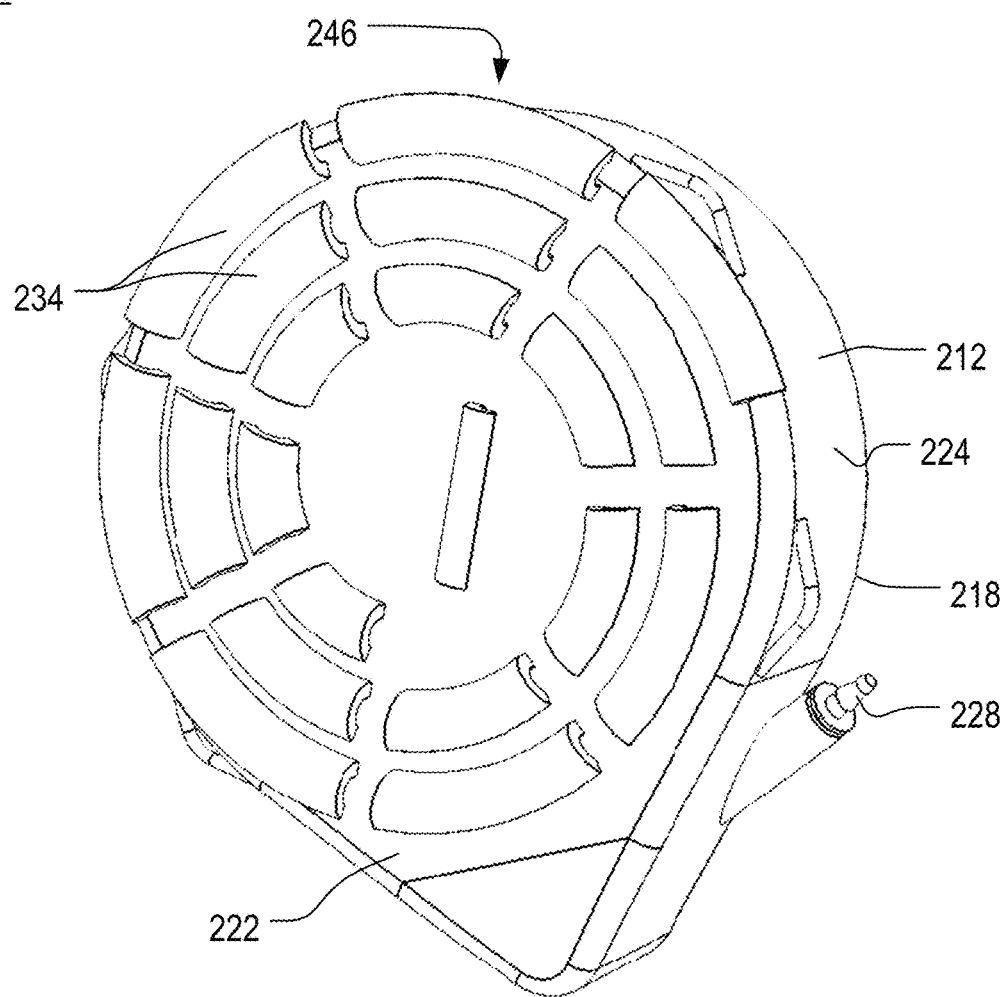
FIG. 9 is a perspective view of the catheter securing device in accordance with another preferred embodiment of the present invention.
Figure 10:
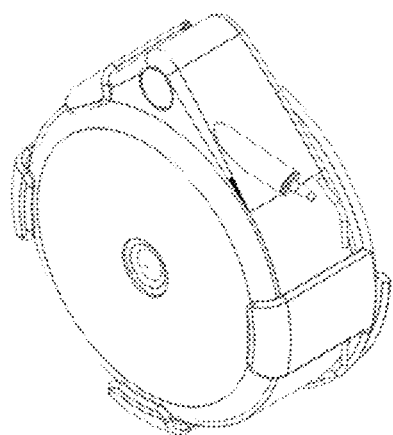
FIG. 10 is another perspective view of the medical delivery device of FIG. 2.
Figure 11:
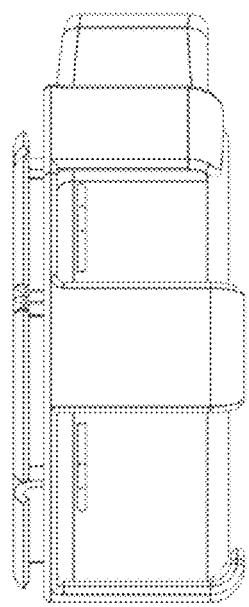
FIG. 11 is a first side elevational view of the medical delivery device of FIG. 10.
Figure 12:
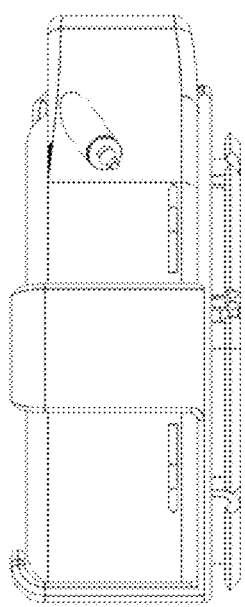
FIG. 12 is a second side elevational view of the medical delivery device of FIG. 10, the view being opposite to the view of FIG. 11.
Figure 13:
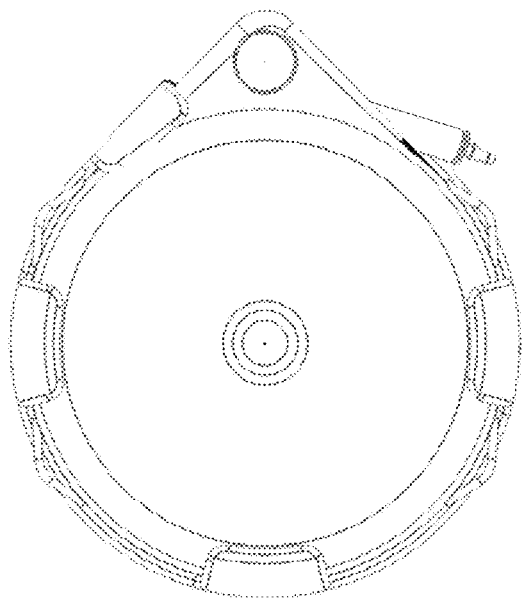
FIG. 13 is a front plan view of the medical delivery device of FIG. 10.
Figure 14:
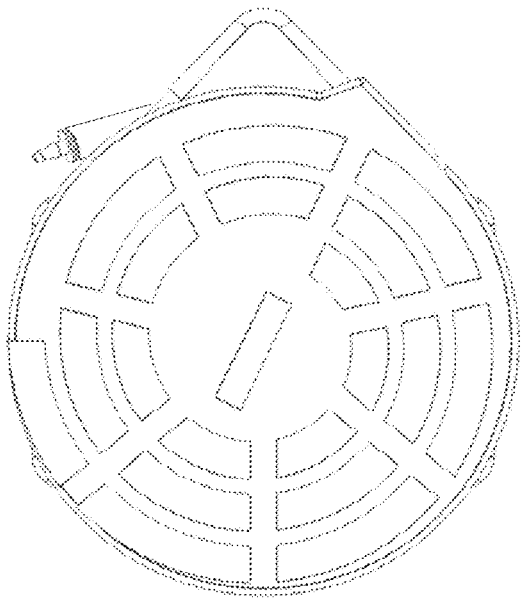
FIG. 14 is a back plan view of the medical delivery device of FIG. 10.
Figure 15:
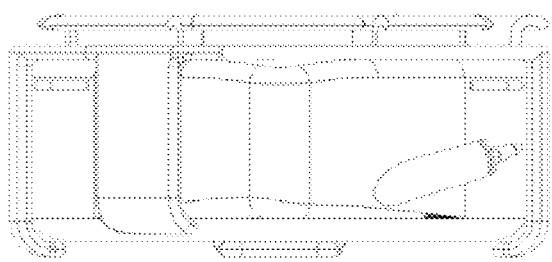
FIG. 15 is a top plan view of the medical delivery device of FIG. 10.
Figure 16:
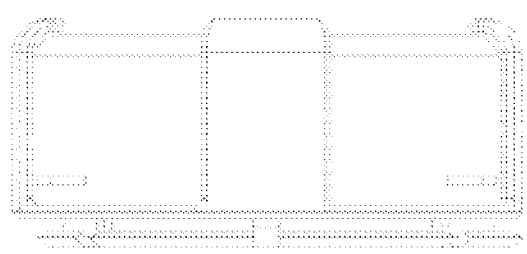
FIG. 16 is a bottom plan view of the medical delivery device of FIG. 10.
Figure 31:
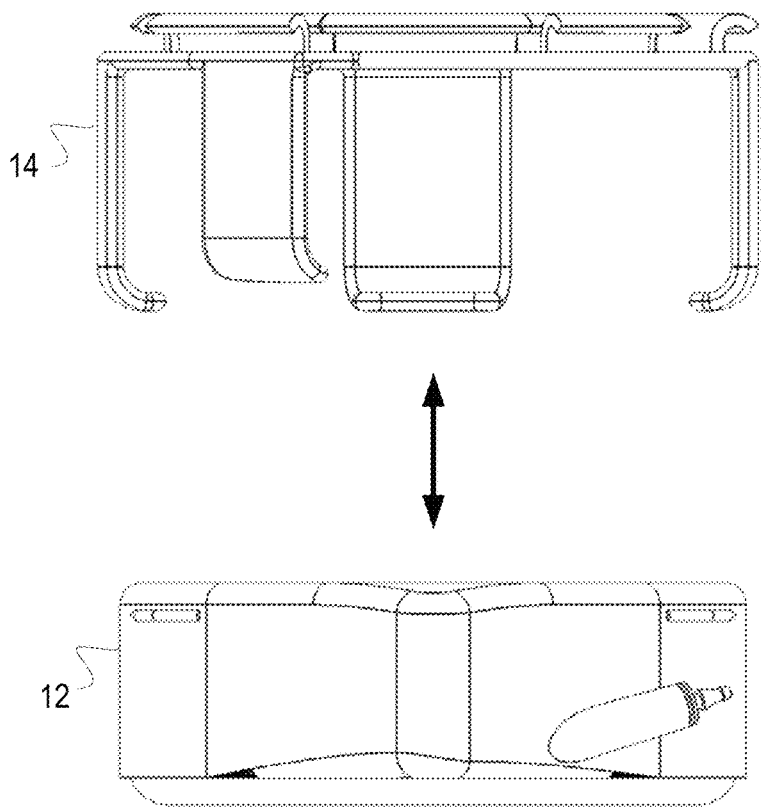
FIG. 31 is a top plan view of the catheter securing device and pump of the medical delivery device of FIG. 10, wherein the catheter securing device and pump are detached and separated from one another and are reattachable together, as indicated by the arrow.
Figure 32:
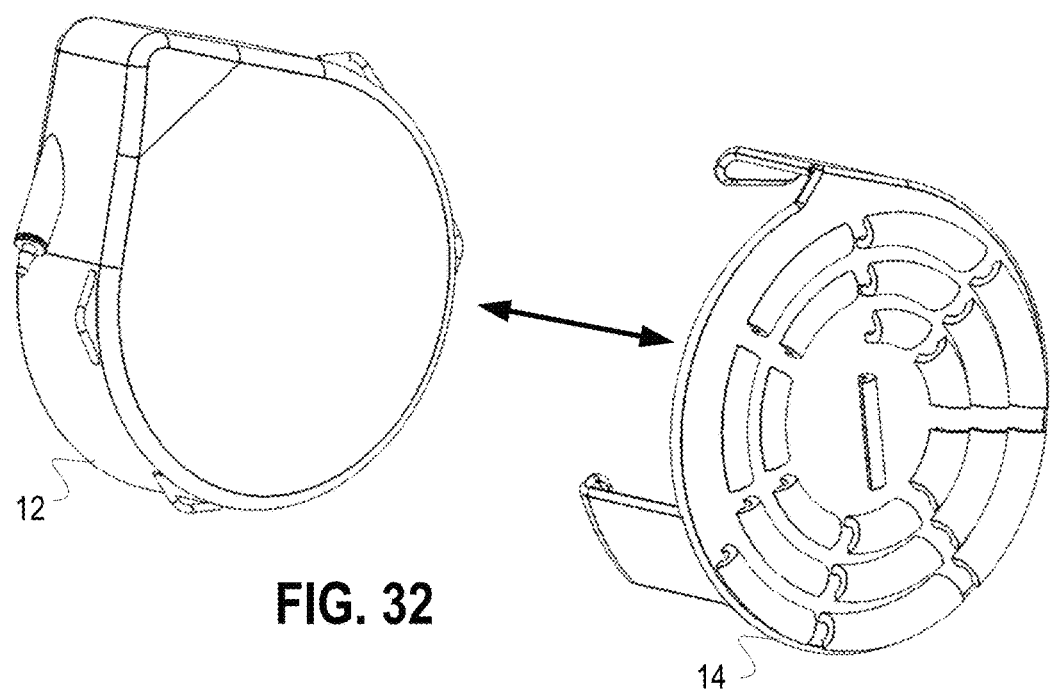
FIG. 32 is a perspective view of the pump and catheter securing device shown in FIG. 31.
Figure 31A:
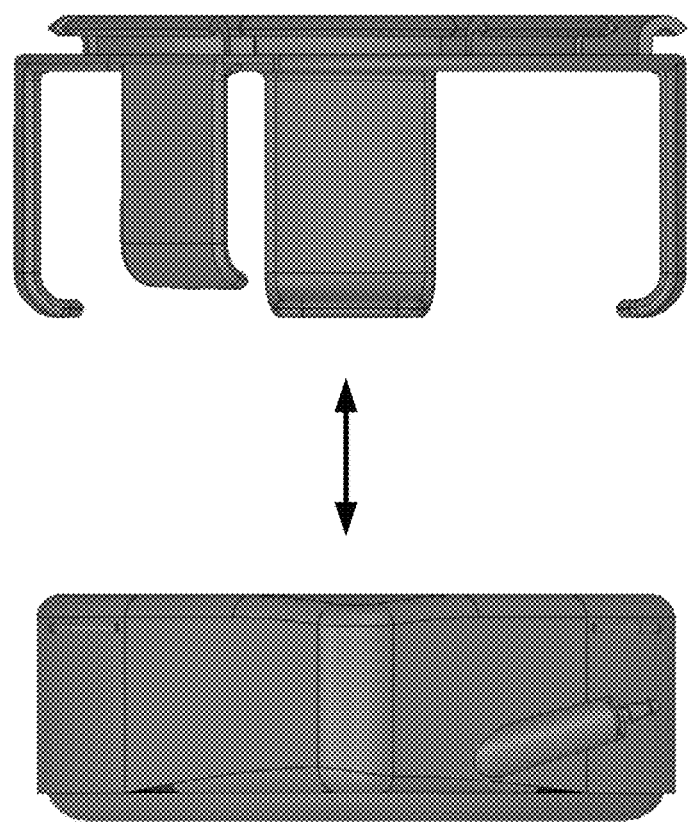
FIG. 31a is a top shaded plan view of the catheter securing device and pump of the medical delivery device of FIG. 10a, wherein the catheter securing device and pump are detached and separated from one another and are reattachable together, as indicated by the arrow.
Figure 32A:
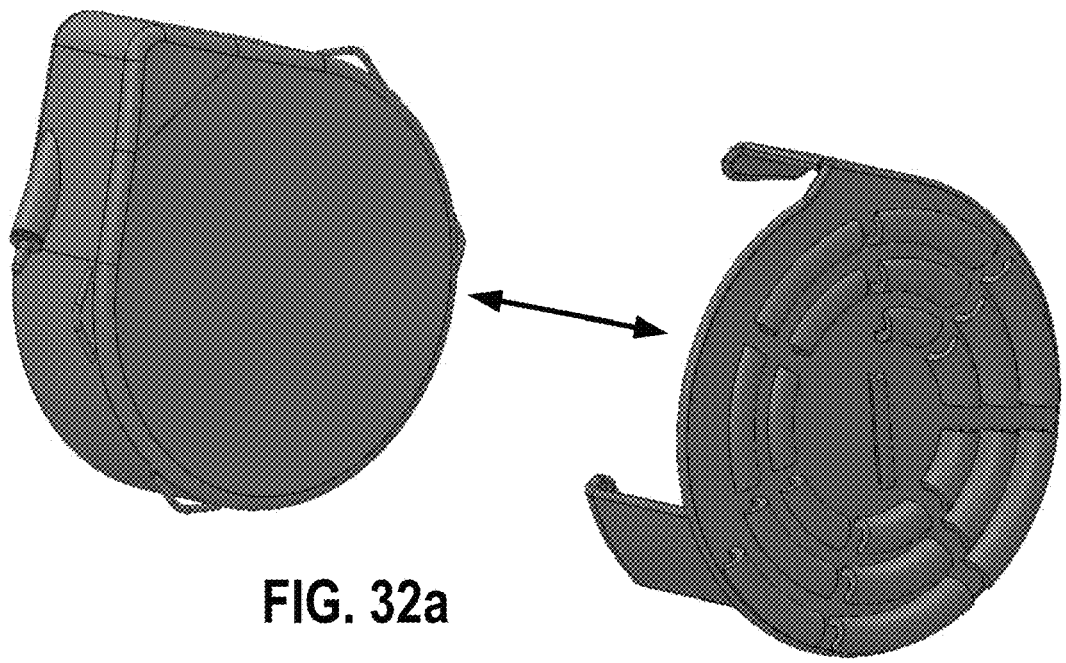
Figure 33:
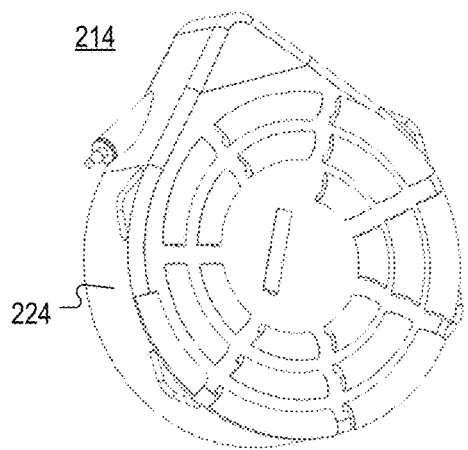
FIG. 33 is a perspective view of the pump of the medical delivery device of FIG. 10.
Figure 34:
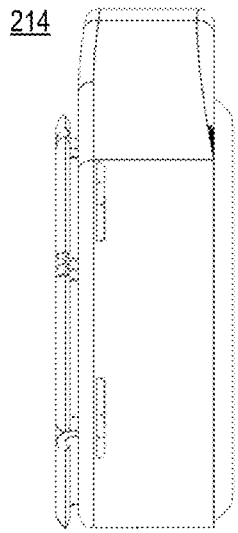
FIG. 34 is a first side elevational view of the pump of FIG. 24.
Figure 35:
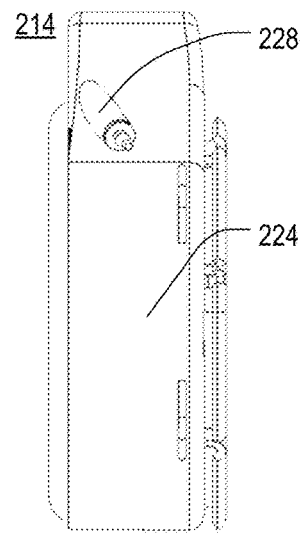
FIG. 35 is a second side elevational view of the pump of FIG. 24, the view being opposite to the view of FIG. 25.
Figure 36:
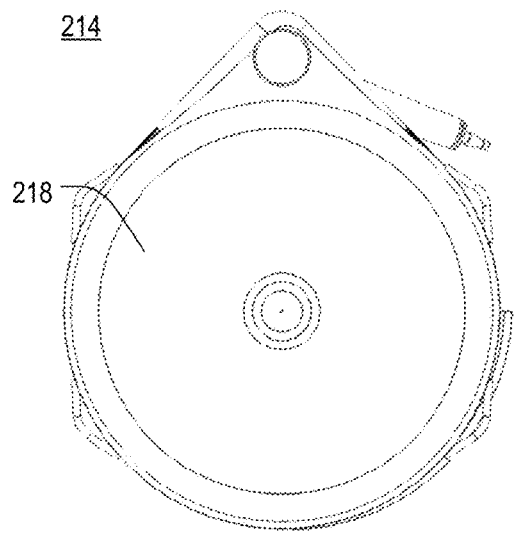
FIG. 36 is a front plan view of the pump of FIG. 24.

FIG. 9 is a perspective view of another preferred embodiment of a medical delivery device 214. As shown, the medical delivery device 214 is similar in operation to the medical delivery device 10 of FIGS. 2 through 8B. The medical delivery device 214 includes a pump 212 with one or more channels 234. As shown in FIG. 9, the pump 212 includes a casing including a front surface 218, a back surface 222, and at least one side wall 224. The front surface 218 of the pump 212 may include a septum to access a chamber (not shown) which holds fluids including, but not limited to, medicine to be dispensed to the body. The at least one side wall 224 of the pump 212 may include a stem 228 to attach a catheter to the pump 212.

Figure 37:
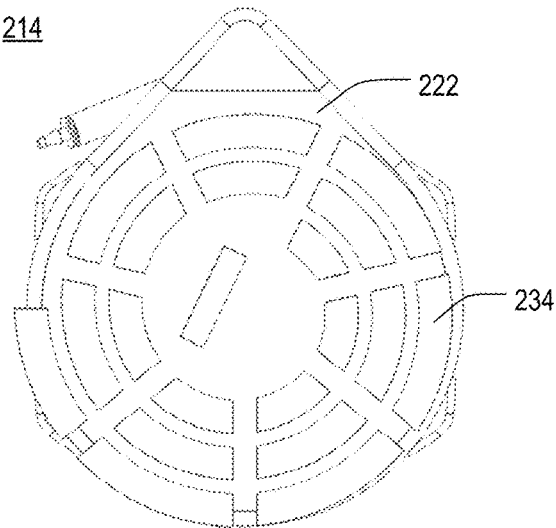
FIG. 37 is a back plan view of the pump of FIG. 24.
Figure 38:
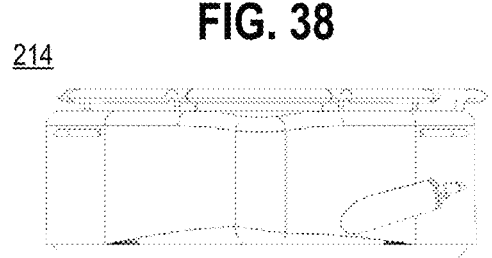
FIG. 38 is a top plan view of the pump of FIG. 24.
Figure 39:
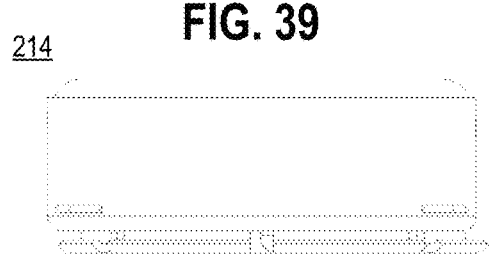
FIG. 39 is a bottom plan view of the pump of FIG. 24.

The back surface 222 of the pump 212 includes the one or more channels 234 incorporated into the back surface 222. As shown in FIG. 37, for example, there are nineteen curved channels 234 of the spiral configuration, with an additional linear channel located proximate a center of the device 214. The one or more channels incorporated into the back surface 222 are configured to hold catheter tubing (not shown). In another contemplated embodiment, the one or more channels are located on the front surface. In another contemplated embodiment, the one or more channels are located on the at least one side wall.

As described with reference to device 10, the one or more channels 234 are configured in the shape of a finger defining recessed opening 246. The size of the opening 246 can vary, but generally the opening 246 preferably is slightly smaller than a diameter of the catheter tubing so that an extent of the tubing can be forced into at least one of the one or more channels and retained there via a tensioned, frictional engagement. The one or more channels also are composed of a sterilizable, flexible and resilient material capable of undergoing elastic deformation during flexing or bending when receiving the catheter tubing. In other contemplated embodiments, the one or more channels comprise a different shape or different configuration. The catheter may occupy all or some of the one or more channels, depending on the extent of excess tubing that is unneeded in an particular use.

Based on the foregoing information, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements; the present invention being limited only by the claims appended hereto and the equivalents thereof.

What is claimed is:

1. A medication delivery device, comprising:
   (a) a casing containing a pump configured to deliver medicine in the form of a fluid, the casing comprising a planar front face, a planar back face, and one or more sidewalls extending between the front face and the back face; and
   (b) catheter tubing extending from the pump and exterior to the casing and defining a fluid pathway for delivering the fluid to a desired anatomical location;
   (c) wherein the casing defines a plurality of channel members protruding outwardly from the back face of the casing in a direction away from the front face, the plurality of channel members being arranged in a concentric spiral configuration about a central area of the back face of the casing with each respective channel member having a greater arc length in a lengthwise direction than any channel member disposed between that respective channel member and the central area such that the plurality of channel members collectively define concentric spirals, and each respective channel member having
      (i) with respect to a plane parallel to the back face, a curved cross-sectional profile that is configured to define part of the spiral configuration, and
      (ii) with respect to a plane orthogonal to the back face that extends through a center of the central area of the back face and widthwise through the respective channel member, a curved cross-sectional profile that
         (A) extends outwardly from the back face of the casing in a direction generally perpendicular to the back face of the casing and then curves such that a distal portion extends at an angle back towards a plane level with the back face of the casing, and
         (B) defines a curved, concave channel opening between that respective channel member and the back face of the casing,
      (iii) wherein a radius of curvature of each channel opening is slightly smaller than a radius of curvature of the catheter tubing such that each channel member is dimensioned to receive and retain an extent of the catheter tubing in a frictional fit therein; and
   (d) wherein the plurality of channel members allow excess catheter tubing that is unneeded to be secured to the plurality of channel members via the frictional fit engagement such that the excess catheter tubing is retained in a kink-free shape corresponding to the spiral configuration in an out-of-the-way position.

2. The medication delivery device of claim 1, wherein the plurality of channel members are defined in an injection-molding manufacturing process of the casing such that the plurality of channel members and the casing consist of a single piece of molded material.

3. A medication delivery device for securing a catheter, comprising:
   (a) a housing containing a pump configured to deliver medicine in the form of a fluid, the housing comprising a planar front surface, a planar back surface, and one or more sidewalls extending between the front surface and the back surface;
   (b) catheter tubing extending from the pump and exterior to the housing and defining a fluid pathway for delivering the fluid to a desired anatomical location;
   (c) a catheter retention member comprising
      (i) a cover wall including a planar outer face and an inner face, and
      (ii) one or more fingers extending from the cover wall in a first direction, the one or more fingers being configured to clip the catheter retention member onto the housing of the pump, and
      (iii) a plurality of channel members protruding outwardly from the outer face of the catheter retention member in a second direction generally opposite the first direction that the one or more fingers extend, the plurality of channel members being arranged in a concentric spiral configuration about a central area of the outer face of the catheter retention member with each respective channel member having a greater arc length in a lengthwise direction than any channel member disposed between that respective channel member and the central area such that the plurality of channel members collectively define concentric spirals, and each respective channel member having (A) with respect to a plane parallel to the outer face, a curved cross-sectional profile that is configured to define part of the spiral configuration, and (B) with respect to a plane orthogonal to the outer face that extends through a center of the central area of the outer face and widthwise through the respective channel member, a curved cross-sectional profile that (I) extends outwardly from the outer face of the catheter retention member in a direction generally perpendicular to the outer face of the catheter retention member and then curves such that a distal portion extends at an angle back towards a plane level with the outer face of the catheter retention member, and (II) defines a curved, concave channel opening between that channel member and the outer face of the catheter retention member, (C) wherein a radius of curvature of each channel opening is slightly smaller than a radius of curvature of the catheter such that each channel member is dimensioned to receive and retain an extent of the catheter tubing in a frictional fit therein;

(d) wherein the plurality of channel members allow excess catheter tubing that is unneeded to be secured to the plurality of channel members via the frictional fit engagement such that the excess catheter tubing is retained in a kink-free shape corresponding to the spiral configuration in an out-of-the-way position.

4. The medication delivery device of claim 3, wherein the one or more fingers comprises at least two fingers configured to clip the catheter retention member to the housing.

5. The medication delivery device of claim 3, wherein the catheter retention member is defined in an injection-molding manufacturing process such that a body of the catheter retention member and the one or more fingers consist of a single piece of molded material.

6. The medication delivery device of claim 3, wherein the plurality of channel members are defined in an injection-molding manufacturing process of the catheter retention member such that the one or more channel members and a body of the catheter retention member consist of a single piece of molded material.

7. The medication delivery device of claim 3, wherein the plurality of channel members comprises a plurality of discontinuous channel members.

8. A medication delivery device providing for storage of excess catheter, comprising:

(a) a pump configured to deliver a fluid to a body, wherein the pump includes a front, a back, and a side wall;

(b) catheter tubing defining a pathway for delivery of the fluid from the pump to a desired anatomical location;

(c) a cover having a planar front surface and a back surface; and (d) at least one finger extending from the cover in a first direction, each at least one finger comprising an extension wall extending from the cover in the first direction and a distal edge portion, and the at least one fingers being configured to secure the cover onto the pump such that the cover may be detached from and reattached to the pump;

(e) wherein the cover includes a plurality of channel members protruding outwardly from the front surface of the cover away from the first direction that the at least one finger extends, the plurality of channel members being arranged in a concentric spiral configuration about a central area of the front surface of the cover with each respective channel member having a greater arc length in a lengthwise direction than any channel member disposed between that respective channel member and the central area such that the plurality of channel members collectively define concentric spirals, and each respective channel member having (i) with respect to a plane parallel to the front surface, a curved cross-sectional profile that is configured to define part of the spiral configuration, and (ii) with respect to a plane orthogonal to the front surface that extends through a center of the central area of the front surface and widthwise through the respective channel member, a finger-shaped curved cross-sectional profile that (A) extends outwardly from the front surface of the cover in a direction generally perpendicular to the front surface of the cover and then curves such that a distal portion extends at an angle back towards a plane level with the front surface of the cover, and (B) defines a curved, concave channel opening between that channel member and the front surface of the cover, (iii) wherein a radius of curvature of each channel opening is slightly smaller than a radius of curvature of the catheter tubing such that each channel member is configured and dimensioned to receive and retain in a frictional fit therein an extent of the catheter tubing; and (f) wherein the plurality of channel members allow excess catheter tubing that is unneeded to be secured to the plurality of channel members via the frictional fit engagement such that the excess catheter tubing is retained in a kink-free shape corresponding to the spiral configuration in an out-of-the-way position.

9. The medication delivery device of claim 8, wherein the pump comprises a septum located at the front of the pump for accessing a chamber for holding the fluid.

10. The medication delivery device of claim 9, wherein the cover is positioned such that the septum is not obstructed.

11. The medication delivery device of claim 8, wherein the pump comprises a stem to connect the pump to the catheter.

12. The medication delivery device of claim 11, wherein the stem is angled to direct the catheter to the plurality of channel members.

13. The medication delivery device of claim 8, wherein the plurality of channel members are defined by structure formed from a flexible and resilient material and undergoes elastic deformation, demonstrating resiliency and flexibility, when the catheter tubing is inserted therein.

14. The medication delivery device of claim 8, wherein the back surface of the cover abuts the back of the pump when the cover is secured to the pump by the at least one finger.

15. The medication delivery device of claim 14, wherein the back surface of the cover is generally planar.

16. The medication delivery device of claim 15, wherein the back surface of the housing of the pump is generally planar.

* * * * *